(12) United States Patent
Chou et al.

(10) Patent No.: US 11,988,664 B2
(45) Date of Patent: May 21, 2024

(54) IMMUNOCHROMATOGRAPHIC DETECTION DEVICE

(71) Applicant: Southern Taiwan University of Science and Technology, Tainan (TW)

(72) Inventors: Ying-Nien Chou, Kaohsiung (TW); Mei-Lian Yao, Kaohsiung (TW)

(73) Assignee: SOUTHERN TAIWAN UNIVERSITY OF SCIENCE AND TECHNOLOGY, Tainan (TW)

(*) Notice: Subject to any disclaimer, the term of this patent is extended or adjusted under 35 U.S.C. 154(b) by 0 days.

(21) Appl. No.: 17/987,181

(22) Filed: Nov. 15, 2022

(65) Prior Publication Data
US 2023/0176046 A1    Jun. 8, 2023

(30) Foreign Application Priority Data
Dec. 7, 2021    (TW) .................... 110145730

(51) Int. Cl.
*G01N 33/543*    (2006.01)
*G01N 33/558*    (2006.01)

(52) U.S. Cl.
CPC ..... *G01N 33/54386* (2013.01); *G01N 33/558* (2013.01)

(58) Field of Classification Search
CPC .......... G01N 33/558; G01N 33/54386; G01N 33/54387; G01N 33/54388; G01N 33/54389; B01L 2300/0825

USPC ....... 422/400, 401, 420, 421, 425, 426, 430; 435/287.7, 287.9, 970, 805, 810; 436/169, 170, 514, 518, 530, 810
See application file for complete search history.

(56) References Cited

FOREIGN PATENT DOCUMENTS

| WO | WO-2013040435 A2 * | 3/2013 | ............. G01N 21/80 |
| WO | WO-2017132604 A1 * | 8/2017 | ........... A61B 5/6826 |
| WO | WO-2020076240 A1 * | 4/2020 | ........... B01D 61/025 |

OTHER PUBLICATIONS

Sivashanmugan, Kundan et al. "An Anti-Fouling Nanoplasmonic SERS Substrate for Trapping and Releasing a Cationic Fluorescent Tag from Human Blood Solution." Nanoscale 9.8 (2017): 2865-2874. (Year: 2017).*

(Continued)

*Primary Examiner* — Christopher L Chin
*Assistant Examiner* — Christina Lusi
(74) *Attorney, Agent, or Firm* — Muncy, Geissler, Olds & Lowe, P.C.

(57) ABSTRACT

An immunochromatographic detection device adapted for detecting an analyte in a specimen includes a surface-modified cellulose membrane, a detection unit, and a substrate. The surface-modified cellulose membrane includes opposite top and bottom surfaces, cellulose fibers, and an anti-biofouling acrylic copolymer that is bonded to the cellulose fibers. The detection unit is disposed on the top surface of the cellulose membrane, is configured to interact with the specimen, and includes a diffusion layer, a capturing layer, a detection layer, a control line layer, and an absorbent layer. The substrate is disposed on the bottom surface of the surface-modified cellulose membrane.

5 Claims, 1 Drawing Sheet

(56) References Cited

OTHER PUBLICATIONS

Liu, Ping-Sheng et al. "Surface Modification of Cellulose Membranes with Zwitterionic Polymers for Resistance to Protein Adsorption and Platelet Adhesion." Journal of membrane science 350.1-2 (2010): 387-394. (Year: 2010).*

Chou YN, Wen TC, Chang Y. Zwitterionic surface grafting of epoxylated sulfobetaine copolymers for the development of stealth biomaterial interfaces. Acta Biomater. Aug. 2016;40:78-91. (Year: 2016).*

* cited by examiner

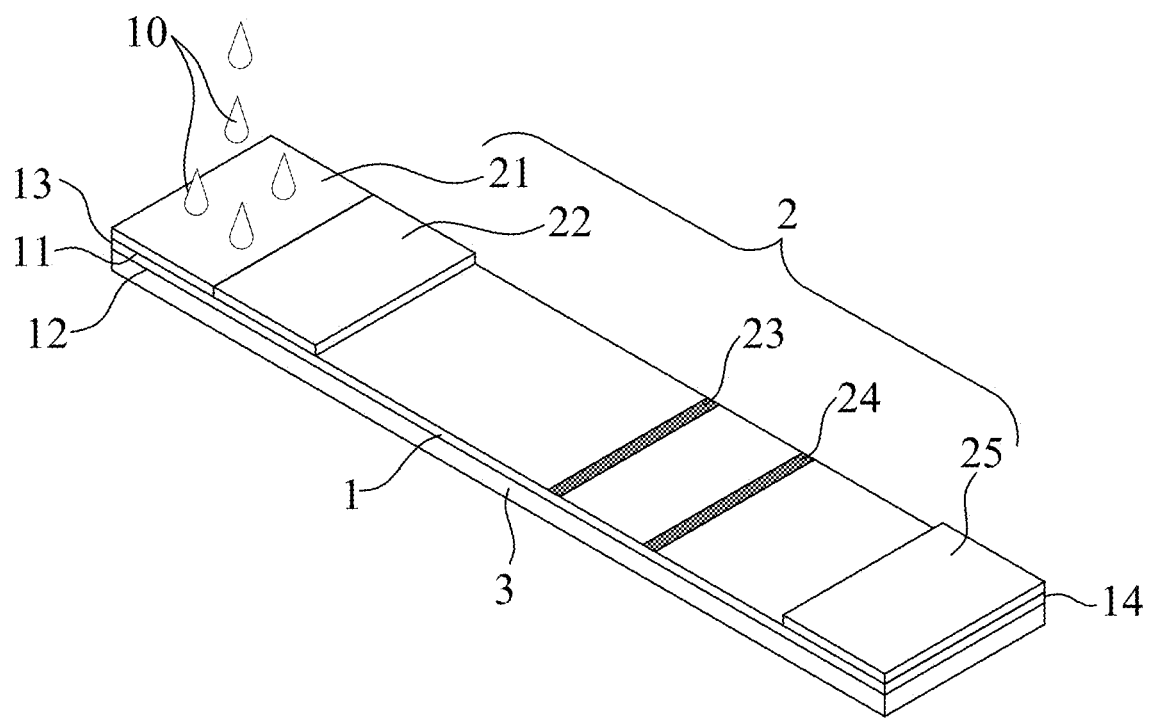

IMMUNOCHROMATOGRAPHIC DETECTION DEVICE

CROSS-REFERENCE TO RELATED APPLICATION

This application claims priority of Taiwanese Invention Patent Application No. 110145730, filed on Dec. 7, 2021.

FIELD

The present disclosure relates to a chromatographic detection device, and more particularly to an immunochromatographic detection device.

BACKGROUND

Use of an immunochromatographic detection device is a common and convenient method for detecting an analyte such as pathogen in a biological specimen, and has been widely applied in clinical screening, customs inspection, forensic identification, etc. In the immunochromatographic detection device, the specificity of antigen or antibody binding to the analyte in the biological specimen serves as a basis of detection, along with gold nanocolloids including gold nanoparticles which serve as a chromogenic reagent to confirm whether the analyte is present in the biological specimen. However, a conventional immunochromatographic detection device includes a cellulose membrane which has a problem that biological molecules easily adheres to a top surface of the cellulose membrane, resulting in poor sensitivity of the conventional immunochromatographic detection device.

SUMMARY

Therefore, an object of the present disclosure is to provide an immunochromatographic detection device which can alleviate at least one of the drawbacks of the prior art.

According to the present disclosure, the immunochromatographic detection device is adapted for detecting an analyte in a specimen and includes a surface-modified cellulose membrane, a detection unit, and a substrate.

The surface-modified cellulose membrane includes opposite top and bottom surfaces, a plurality of cellulose fibers, and an anti-biofouling acrylic copolymer. The top surface has opposite first and second end portions. The anti-biofouling acrylic copolymer is bonded to the cellulose fibers, and is made from a first compound and a second compound.

The first compound is selected from the group consisting of glycidyl methacrylate, hydroxyethylmethacrylate, $CH_2=C(CH_3)-C(O)-O-CH_2-C(O)H$, and combinations thereof. The second compound is selected from the group consisting of sulfobetaine methacrylate, sulfobetaine acrylamide, and a combination thereof.

The detection unit is disposed on the top surface of the cellulose membrane, is configured to interact with the specimen after the specimen diffuses into the surface-modified cellulose membrane, and sequentially includes, in a direction from the first end portion towards the second end portion, a diffusion layer, a capturing layer, a detection layer, a control line layer, and an absorbent layer.

The diffusion layer is for receiving and diffusing the specimen. The capturing layer is connected to the diffusion layer, and includes a main body and a plurality of gold nanocolloids releasably disposed on the main body. Each of the gold nanocolloids includes a gold nanoparticle and a first binding agent loaded on the gold nanoparticle for specifically binding to the analyte so as to form a complex.

The detection layer is spaced apart from the capturing layer, and includes a second binding agent for specifically binding to the analyte of the complex. The control line layer is spaced apart from the detection layer, and includes a third binding agent for specifically binding to the gold nanocolloids. The absorbent layer is spaced apart from the control line layer, and is adapted for absorbing the specimen after the specimen passes through the control line layer.

The substrate is disposed on the bottom surface of the surface-modified cellulose membrane.

BRIEF DESCRIPTION OF THE DRAWINGS

Other features and advantages of the present disclosure will become apparent in the following detailed description of the embodiments with reference to the accompanying drawings, of which:

The sole FIGURE is a perspective view of an embodiment of an immunochromatographic detection device according to the present disclosure.

DETAILED DESCRIPTION

Before the present invention is described in greater detail, it should be noted that where considered appropriate, reference numerals or terminal portions of reference numerals have been repeated among the figures to indicate corresponding or analogous elements, which may optionally have similar characteristics.

Referring to the sole FIGURE, an embodiment of an immunochromatographic detection device of the present disclosure is adapted for detecting an analyte in a specimen 10 and includes a surface-modified cellulose membrane 1, a detection unit 2, and a substrate 3.

The specimen 10 may be, for example, human body fluids, such as blood, urine, saliva, nasal discharge, etc. The analyte may be, for example, a biological analyte such as carcinoembryonic antigen (CEA) or fibrinogen, but is not limited thereto.

The surface-modified cellulose membrane 1 includes opposite top and bottom surfaces 11, 12, a plurality of cellulose fibers, and an anti-biofouling acrylic copolymer bonded to the cellulose fibers. The top surface 11 of the surface-modified cellulose membrane 1 has opposite first and second end portions 13, 14.

The anti-biofouling acrylic copolymer is made from a first compound and a second compound through a polymerization reaction. The first compound is selected from the group consisting of glycidyl methacrylate, hydroxyethylmethacrylate, $CH_2=C(CH_3)-C(O)-O-CH_2-C(O)H$, and combinations thereof. The second compound is selected from the group consisting of sulfobetaine methacrylate, sulfobetaine acrylamide, and a combination thereof. The anti-biofouling acrylic copolymer is firmly bonded to the cellulose fibers through the epoxy groups, hydroxyl groups, and aldehyde groups of the first and second compounds. By including the anti-biofouling acrylic copolymer, during the diffusion and movement of the specimen 10 on the surface-modified cellulose membrane 1, the analyte in the specimen 10 can be prevented from adhering to the top surface 11 of the surface-modified cellulose membrane 1, so as to avoid the problem that the immunochromatographic detection device may fail to detect the analyte (i.e., the detection accuracy and sensitivity of the immunochromatographic detection device may be therefore improved).

A molar ratio of the first compound to the second compound in the anti-biofouling acrylic copolymer may range from 1:4 to 4:1, so as to improve the sensitivity of the immunochromatographic detection device of the present disclosure.

The detection unit 2 is disposed on the top surface 11 of the surface-modified cellulose membrane 1, and is configured to interact with the specimen 10 after the specimen 10 diffuses into the surface-modified cellulose membrane 1.

The detection unit 2 sequentially includes, in a setting direction from the first end portion 13 towards the second end portion 14, a diffusion layer 21, a capturing layer 22, a detection layer 23, a control line layer 24, and an absorbent layer 25.

The diffusion layer 21 is configured to receive the specimen 10 and diffuse the specimen 10 towards the capturing layer 22. The diffusion layer 21 may be, for example, a cellulose paper or a nitrocellulose membrane. In this embodiment, the diffusion layer 21 is a cellulose paper.

The capturing layer 22 is connected to the diffusion layer 21, and includes a main body and a plurality of gold nanocolloids releasably disposed on the main body. The main body may be, e.g., a cellulose paper. Each of the gold nanocolloids includes a gold nanoparticle and a first binding agent loaded on the gold nanoparticle for specifically binding to the analyte so as to form a complex. The first binding agent may be, for example, an antigen, an antibody, or the like.

In this embodiment, the first binding agent is an antibody capable of binding to the analyte. If the analyte is present in the specimen 10, a portion of the gold nanocolloids will capture and bind to the analyte to form the complex. The resultant complex and another portion of the gold nanocolloids that is not binding to the analyte will be released from the main body and will be diffused together with the specimen 10 in the setting direction on the top surface 11 of the surface-modified cellulose membrane 1. If the specimen 10 is free from the analyte, the gold nanocolloids (without formation of the complex) will be released from the main body and will be diffused together with the specimen 10 in the setting direction on the top surface 11 of the surface-modified cellulose membrane 1.

The detection layer 23 is spaced apart from the capturing layer 22, and includes a second binding agent for specifically binding to the analyte of the complex. The second binding agent may be, for example, an antigen, an antibody, or the like. In this embodiment, the second binding agent is a primary antibody. When the specimen 10 containing the analyte forming the complex with the gold nanocolloids are diffused into the detection layer 23, the second binding agent will bind to the analyte of the complex, causing the detection layer 23 to produce a color change. When the specimen 10 free from the analyte and the gold nanocolloids without the formation of the complex are diffused into the detection layer 23, the second binding agent will not bind to the gold nanocolloids, and thus, no color change will occur. In this embodiment, the second binding agent is colorless, and when the second binding agent binds to the analyte of the complex, the color of the detection layer 23 changes into red due to the presence of the gold nanoparticles of the gold nanocolloids.

The control line layer 24 is spaced apart from the detection layer 23, and includes a third binding agent for specifically binding to the gold nanocolloids. The third binding agent may be, for example, an antigen, an antibody, or the like. In this embodiment, the third binding agent is a secondary antibody capable of binding to the first binding agent. When the specimen 10 and the gold nanocolloids are diffused into the control line layer 24, the third binding agent will bind to the first binding agent of the gold nanocolloids, causing the control line layer 24 to produce a color change. In this embodiment, the third binding agent is colorless, and when the third binding agent binds to the gold nanocolloids, the color of the control line layer 24 changes into red.

The absorbent layer 25 is spaced apart from the control line layer 24, and is adapted for absorbing the specimen 10 after the specimen 10 passes through the control line layer 24. The absorbent layer 25 may be, for example, a cellulose paper or a cotton pad. In this embodiment, the absorbent layer 25 is a cellulose paper.

The substrate 3 is disposed on the bottom surface 12 of the surface-modified cellulose membrane 1. Examples of a material for making the substrate 3 include, but are not limited to, polyethylene terephthalate, polypropylene and a combination thereof. In this embodiment, the substrate is made of polypropylene.

The present disclosure will be further described by way of the following examples. However, it should be understood that the following examples are intended solely for the purpose of illustration and should not be construed as limiting the present disclosure in practice.

Examples 1 to 10 (E1-E10)

Each of the immunochromatographic detection devices of E1 to E10 has a configuration as described in the above embodiment and shown in the sole FIGURE, and the difference among E1 to E10 resides in the types and/or amounts of the first and second compounds used in the preparation of the anti-biofouling acrylic copolymer of the surface-modified cellulose membrane 1.

To be specific, in E1, the first compound is glycidyl methacrylate, the second compound is sulfobetaine methacrylate, and the molar ratio of the first compound to the second compound in the anti-biofouling acrylic copolymer is 2:3. A method for preparing the surface-modified cellulose membrane 1 includes the following steps.

In step A, 0.02 g of azobisisobutyronitrile was mixed with 5.126 mL of methanol to form a first solution, while 1.021 g (0.003654 mol) of the second compound (i.e., sulfobetaine methacrylate) was mixed with 1.709 mL of water to form a second solution. Next, the first and second solutions were mixed with 332.3 µL (0.002436 mol) of the first compound (i.e., glycidyl methacrylate, GMA), and then subjected to a polymerization reaction by heating to 60° C. for 6 hours in a nitrogen atmosphere, so as to form a first mixture including the anti-biofouling acrylic copolymer, in which the molar ratio of glycidyl methacrylate to sulfobetaine methacrylate (SBMA) was 2:3. Thereafter, the first mixture was cooled in ice bath at 0° C. for 30 minutes, so as to obtain a second mixture. Then, methanol was added into the second mixture such that the anti-biofouling acrylic copolymer was precipitated from the second mixture. After a filtration process, the thus obtained anti-biofouling acrylic copolymer was dried in a vacuum oven and then in a freeze dryer.

In step B, 20 mg of the dried anti-biofouling acrylic copolymer, 200 µL of ammonia (serving as catalyst), and 20 mL of water were mixed to form a copolymer solution having a pH value of about 11 in which the concentration of the anti-biofouling acrylic copolymer is 1 mg/mL. Next, a cellulose membrane was immersed in the copolymer solution, and heated to 70° C. in a rocking oven for 15 hours at a rotational speed of 110 rpm, such that the anti-biofouling acrylic copolymer bonds to the cellulose fibers of the cellulose membrane, thereby obtaining the surface-modified cellulose membrane 1.

In E2, the second solution used in step A as mentioned above was formed by mixing 0.732 g (0.00263 mol) of sulfobetaine acrylamide (replacing sulfobetaine methacrylate used in E1) with 3.68 mL of water.

In E3, the first compound used in step A as mentioned above to be mixed with the first and second solutions was 304.23 μL (0.002435 mol) of hydroxyethylmethacrylate (replacing glycidyl methacrylate used in E1).

In E4, the second solution used in step A as mentioned above was formed by mixing 0.7318 g (0.00263 mol) of sulfobetaine acrylamide (replacing sulfobetaine methacrylate) with 3.679 mL of water.

In E5, the first compound used in step A as mentioned above to be mixed with the first and second solutions was 280.5265 μL (0.002436 mol) of $CH_2=C(CH_3)-C(O)-O-CH_2-C(O)H$ (replacing glycidyl methacrylate).

In E6, the second solution used in step A as mentioned above was formed by mixing 0.7318 g (0.00263 mol) of sulfobetaine acrylamide (replacing sulfobetaine methacrylate used in E1) with 5.1108 mL of water.

In E7, the second and first compounds used in step A as mentioned above were 1.36 g (0.0049 mol) of sulfobetaine methacrylate, and 166.15 μL (0.00122 mol) of glycidyl methacrylate, and the molar ratio of glycidyl methacrylate to sulfobetaine methacrylate in the first mixture was 1:4.

In E8, the second and first compounds used in step A as mentioned above were 1.19 g (0.0043 mol) of sulfobetaine methacrylate and 249.23 μL (0.0018 mol) of glycidyl methacrylate, and the molar ratio of glycidyl methacrylate to sulfobetaine methacrylate in the first mixture was 3:7.

In E9, the second and first compounds used in step A as mentioned above were 0.68 g (0.0024 mol) of sulfobetaine methacrylate and 498.46 μL (0.0037 mol) of glycidyl methacrylate, and the molar ratio of glycidyl methacrylate to sulfobetaine methacrylate in the first mixture was 6:4.

In E10, the second and first compounds used in step A as mentioned above were 0.34 g (0.0012 mol) of sulfobetaine methacrylate and 664.61 μL (0.0049 mol) of glycidyl methacrylate, and the molar ratio of glycidyl methacrylate to sulfobetaine methacrylate in the first mixture was 4:1.

Comparative Example 1 (CE1)

In order to compare the sensitivity of the immunochromatographic detection devices of E1 to E10, an immunochromatographic detection device of CE1 was prepared. The immunochromatographic detection device of CE1 is generally similar to that of E1, except that the surface-modified cellulose membrane 1 of CE1 does not include the anti-biofouling acrylic copolymer.

Property Evaluations
1. Evaluation of Anti-Biofouling Properties

The surface-modified cellulose membrane 1 of each of the immunochromatographic detection devices of E1, E7 to E10 and CE1, serving as a test sample, was subjected to evaluation of anti-biofouling properties using three different bioanalytes including bovine serum albumin (BSA), recombinant human lysozyme and human fibrinogen. The procedures are described below.

Each of the test samples was placed into 1.0 mL of phosphate-buffered saline (PBS), and then placed in a hot air circulating oven at 37° C. for 6 hours. After removal of PBS, the test sample was rinsed 3 times with fresh PBS. Next, the test sample was immersed in 1.0 mL of a bioanalyte solution, i.e., a BSA solution (Manufacturer: Sigma-Aldrich; Catalogue no.: A7030), a recombinant human lysozyme solution (Manufacturer: Sigma-Aldrich; Catalogue no.: L1667) or a human fibrinogen solution (Manufacturer: Sigma-Aldrich; Catalogue no.: 7694-250), and then placed in the hot air circulating oven at 37° C. for 30 minutes. After that, the bioanalyte solution was aspirated from the test sample using a pipette, followed by rinsing 3 times with fresh PBS. Thereafter, the test sample on which the bioanalyte may adhere was immersed in 1.0 mL of a color-developing solution containing bicinchoninic acid (BCA) (Manufacturer: Visual Protein; Catalogue no.: BC03-500), and then placed in the hot air circulating oven at 37° C. for 30 minutes. After that, 200 μL of the resultant solution containing the bioanalyte was aspirated from the test sample using the pipette and transferred into a 96-well plate, and then subjected to light absorbance measurement at a wavelength of 562 nm ($OD_{562}$) using a microplate spectrophotometer (Manufacturer: BMG Labtech; Model no.: SPECTROstar® Nano), so as to determine the amount of the bioanalyte (mg/mL) adhering to the top surface of the test sample. Relative bioanalyte adhesion percentage on the test sample can be calculated by substituting the light absorbance into the following formula:

$$A=(B/C)\times 100 \quad (1)$$

where A=relative bioanalyte adhesion percentage (%)
B=$OD_{562}$ of a respective one of the test samples of E1, E7 to E10, and CE1
C=$OD_{562}$ of the test sample of CE1

The results are shown in Table 1 below. The lower the determined relative bioanalyte adhesion percentage is, the higher the anti-biofouling property of the test sample is (i.e., the surface-modified cellulose membrane 1 is more resistant to adhesion of the bioanalyte).

2. Determination of Sensitivity

First, 1 μL of anti-human fibrinogen antibody (Manufacturer: Arigo Biolaboratories; Catalogue no.: ARG10362) was added to 1 mL of gold nanoparticle suspension (Manufacturer: Tripod Nano Technology Corporation; Catalogue no.: AP-Au40) having a pH value of 6 under shaking at 70 rpm and 27° C. for 30 minutes using a rotary shaker, so as to form a first mixture in which the anti-human fibrinogen antibody binds to the gold nanoparticles. Next, the first mixture was subjected to a blocking treatment using 100 μL of a BSA solution (50 mg/mL) under rotation at a speed of 70 rpm for 30 minutes. The resultant product was subjected to, centrifugation at 4° C. under a relative centrifugal force (rcf) of 1250 g for 20 minutes, and then under a rcf of 9600 g. The resultant supernatant was aspirated out, and resuspended with 1 mL of PBS and 200 μL of a BSA solution (10 mg/mL) form a second mixture, which was then added into a 96-well plate (50 μL/well).

Four surface-modified cellulose membranes 1 of each of E1 and CE1 serving as test samples were prepared. For each of the test sample, a center part of the top surface thereof was coated with a respective one of human fibrinogen solutions having different concentration (1 mg/mL, 0.5 mg/mL, 0.1 mg/mL and 0.05 mg/mL), and then dried in an oven at 37° C. Afterwards, the test samples coated with human fibrinogen were vertically placed in the wells of the 96-well plate each containing the second mixture for 180 seconds, so as to allow the second mixture in the wells to be upwardly diffused into the test samples, and to allow the anti-human fibrinogen antibody of the second mixture to be bound to the human fibrinogen on the central part of the surface-modified cellulose membranes 1. The sensitivity of each test sample was determined by converting RGB images to grayscale using the formula gray=(red+green+blue)÷3 using ImageJ software installed on a computer (Manufacturer: Asus; Model: VivoBook 15). The aforesaid experiment was repeated using gold nanoparticle suspensions respectively having pH values of 7, 8, 9, and 10. The results are shown in Table 2 below.

TABLE 1

| Surface-modified cellulose membrane | Anti-biofouling acrylic copolymer | | Relative bioanalyte adhesion amount (%) | | |
|---|---|---|---|---|---|
| | GMA (molar ratio) | SBMA (molar ratio) | BSA | Human recombinant lysozyme | Human fibrinogen |
| E1 | 40 | 60 | 49.91 | 59.85 | 25.06 |
| E7 | 20 | 80 | 62.26 | 74.10 | 51.81 |
| E8 | 30 | 70 | 69.67 | 77.76 | 27.54 |
| E9 | 60 | 40 | 65.50 | 81.32 | 27.72 |
| E10 | 80 | 20 | 67.93 | 80.68 | 40.03 |
| CE1 | — | — | 100 | 100 | 100 |

"—": not added

As shown in Table 1, in comparison with the surface-modified cellulose membrane 1 of CE1, the surface-modified cellulose membranes 1 of E1 and E7 to E10 including the anti-biofouling acrylic copolymer are capable of reducing the amount of the bioanalyte which adheres to the top surface of the surface-modified cellulose membranes 1.

TABLE 2

| Surface-modified cellulose membrane | pH of gold nanoparticles suspension | Concentration of human cellulose protein (mg/mL) | | | |
|---|---|---|---|---|---|
| | | 1.0 | 0.5 | 0.1 | 0.05 |
| | | Sensitivity level: grayscale value (%) | | | |
| E1 | 6 | 5.92 | 4.29 | 1.77 | 1.56 |
| | 7 | 4.53 | 4.39 | 0.22 | 0.07 |
| | 8 | 6.73 | 6.37 | 4.79 | 2.03 |
| | 9 | 5.63 | 5.16 | 3.10 | 2.36 |
| | 10 | 5.85 | 3.99 | 0 | 0 |
| CE1 | 6 | 5.48 | 3.65 | 0.36 | 0 |
| | 7 | 1.33 | 1.23 | 0 | 0 |
| | 8 | 5.81 | 4.64 | 2.13 | 0 |
| | 9 | 4.16 | 2.87 | 1.67 | 0 |
| | 10 | 2.72 | 2.21 | 0 | 0 |

As shown in Table 2, in comparison with CE1, the immunochromatographic detection device of E1 including the anti-biofouling acrylic copolymer is capable of detecting the human fibrinogen having low concentration (e.g., not greater than 1.0 mg/mL) with stronger signal intensity, even down to a concentration of 0.1 mg/mL or 0.05 mg/mL. As such, the immunochromatographic detection device of the present disclosure indeed has an excellent sensitivity.

In summary, by having the anti-biofouling acrylic polymer bonded to the cellulose fibers, an analyte to be detected in the specimen 10 can be prevented from adhering to the top surface 11 of the surface-modified cellulose membrane 1, thereby enhancing the detection sensitivity of the immunochromatographic detection device of the present disclosure.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, FIGURE, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. An immunochromatographic detection device adapted for detecting an analyte in a specimen, comprising:
    a surface-modified cellulose membrane that includes opposite top and bottom surfaces, said top surface having opposite first and second end portions, a plurality of cellulose fibers, and
        an anti-biofouling acrylic copolymer which is bonded to said cellulose fibers using ammonia as a catalyst and which is made from a first compound and a second compound, said first compound being selected from the group consisting of glycidyl methacrylate, hydroxyethylmethacrylate, $CH_2{=}C(CH_3){-}C(O){-}O{-}CH_2{-}C(O)H$, and combinations thereof, and said second compound being selected from the group consisting of sulfobetaine methacrylate, sulfobetaine acrylamide, and a combination thereof, wherein a molar ratio of said first component to said second component in said anti-biofouling acrylic copolymer ranges from 30:70 to 80:20;
    a detection unit that is disposed on said top surface of said surface-modified cellulose membrane, that is configured to interact with the specimen after the specimen diffuses into said surface-modified cellulose membrane, and that sequentially includes, in a direction from said first end portion towards said second end portion,
        a diffusion layer for receiving and diffusing the specimen,
        a capturing layer connected to said diffusion layer and including a main body and a plurality of gold nanocolloids releasably disposed on said main body, each of said gold nanocolloids including a gold nanoparticle and a first binding agent loaded on said gold nanoparticle for specifically binding to the analyte so as to form a complex,
        a detection layer spaced apart from said capturing layer and including a second binding agent for specifically binding to the analyte of the complex,
        a control line layer spaced apart from said detection layer and including a third binding agent for specifically binding to said gold nanocolloids, and
        an absorbent layer spaced apart from said control line layer and adapted for absorbing the specimen after the specimen passes through said control line layer; and a substrate disposed on said bottom surface of said surface-modified cellulose membrane.

2. The immunochromatographic detection device as claimed in claim 1, wherein said first compound is glycidyl methacrylate.

3. The immunochromatographic detection device as claimed in claim 1, wherein said second compound is sulfobetaine methacrylate.

4. The immunochromatographic detection device as claimed in claim 1, wherein each of said first, second and third binding agents are one of either an antigen or an antibody.

5. The immunochromatographic detection device as claimed in claim 1, wherein said first compound is $CH_2=C(CH_3)-C(O)-O-CH_2-C(O)H$.

* * * * *